United States Patent [19]

Krakow

[11] 3,976,883

[45] Aug. 24, 1976

[54] INFRARED ANALYZER

[75] Inventor: Burton Krakow, Waltham, Mass.

[73] Assignee: Honeywell Inc., Minneapolis, Minn.

[22] Filed: May 10, 1973

[21] Appl. No.: 359,162

[52] U.S. Cl. .................................. 250/343; 250/373
[51] Int. Cl.² ........................................ G01H 21/26
[58] Field of Search ........... 250/339, 343, 344, 345, 250/346, 373

[56] References Cited
UNITED STATES PATENTS

| | | | |
|---|---|---|---|
| 2,721,942 | 10/1955 | Friel | 250/346 |
| 2,758,215 | 8/1956 | Skarstrom | 250/346 |
| 3,435,209 | 3/1969 | Keahl | 250/339 |
| 3,539,804 | 11/1970 | Illetdeaux | 250/339 |
| 3,562,522 | 2/1971 | Cederstrand | 250/343 |

Primary Examiner—Craig E. Church
Attorney, Agent, or Firm—Charles G. Mersereau; Henry L. Hanson

[57] ABSTRACT

A non-dispersive infrared correlation spectrometer for determining the presence of a gas having a known characteristic infrared absorption spectrum in a gaseous mixture is disclosed which utilizes a unique combination filtering system in cooperation with a highly sensitive solid state detector which provide a highly selective and sensitive instrument.

16 Claims, 1 Drawing Figure

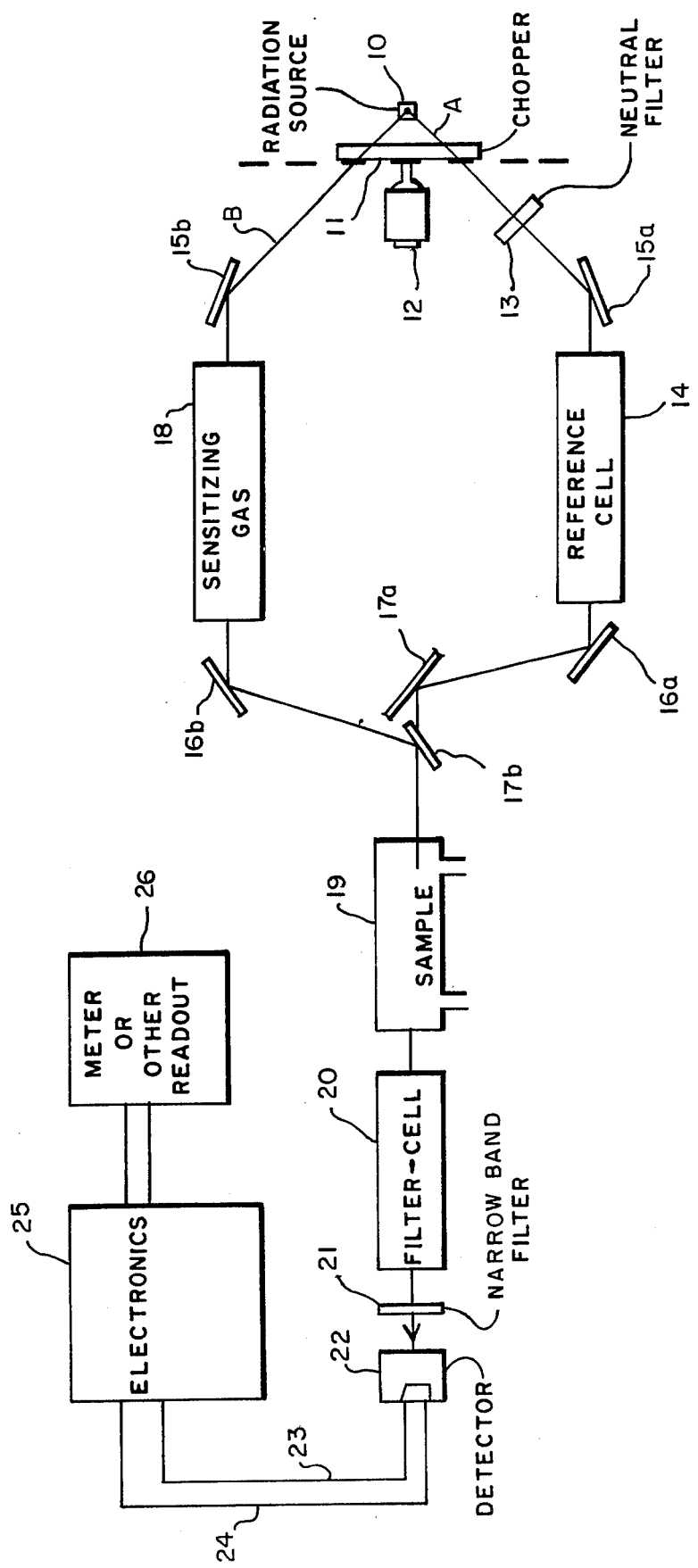

INFRARED ANALYZER

BACKGROUND OF THE INVENTION

1. Field of the Invention

The present invention relates generally to the analysis of gases by the use of infrared radiation and, more particularly, to a non-dispersive infrared correlation spectrometer having a high degree of sensitivity and specificity.

2. Description of the Prior Art

It is well known in the art to employ the principle of absorption of infrared radiation in a gas mixture as the basis for qualitative analysis of the mixture and, in particular, for the quantitative determination of the presence of one or more specific constituents in that mixture. Such instruments possess great practical potential in monitoring industrial effluent and process streams, exhaust analysis and other important environmental and ecological considerations.

In one type of analyzer, the infrared energy absorbed from a reference beam is compared with that absorbed from an analysis beam sensitized with the "gas of interest" (i.e., the gas sought to be determined in the sample) in a manner which renders the difference between the energy absorbed from each of the two beams dependent only upon the amount of the specific gas of interest present in the sample. Thus, the reference beam traverses a cell filled with a gas which does not absorb infrared radiation and a sample cell which may or may not contain the gas of interest and proceeds finally to a detector which produces a signal in response to the amount of infrared radiation received. The signal produced by the absorption from this beam is then compared with the signal produced by the absorption from a second or analysis beam which traverses a sensitizing cell containing the gas of interest and the sample cell and impinges on the detector. Both of these beams may be passed through additional filter cells in which an interfering gas, one which has infrared absorption spectrum overlapping the infrared absorption spectrum of the gas of interest, may be placed to filter out the effect of that particular component if such exists in the sample. The detector used may be of any type suitable for the absorption of infrared in the spectral range required.

One great problem associated with all of these prior art devices is concerned with the inability to develop an analyzing technique which does away with the detection problems caused by interfering gases in the sample and, at the same time, provides a fast, accurate quantitative determination of the gas of interest which is independent of fluctuations in the source output and detector absorption. Another problem concerned with quantitative accuracy in prior art devices is in the detection of small quantities of a gas of interest. A small difference in two relatively intense beams must be measured and even a small error in this situation can produce a large error in the quantitative measurement.

SUMMARY OF THE INVENTION

According to the present invention, an improved non-dispersive infrared analyzer is provided which overcomes problems associated with specificity, essentially eliminates errors resulting from source output and detector absorption fluctuation and provides enhanced sensitivity by the use of special filtering and detection techniques. The analyzer of the invention is basically a correlation spectrometer which electronically compares electrical signals produced by the absorption of infrared radiation from a source traversing analysis and reference optical systems.

The reference optical system of the analyzer includes a first or reference filter cell, the sample cell, a narrow bandpass optical filter and second filter cell between the source and the detector. The analysis optical system includes a sensitizing cell, the sample cell, a narrow bandpass optical filter and a second filter cell between the source and the detector.

In the reference optical system, the first or reference filter cell is one containing a gas transparent to infrared radiation and the sample cell contains a sample of the gas to be analyzed. The narrow bandpass optical filter is one which filters out the entire infrared spectrum with the exception of a narrow band of wavelengths which contains at least one strong absorption line of the particular gas of interest. The second filter cell is one which may contain a gas having an infrared absorption spectrum which overlaps that of the gas of interest in the narrow band passed by the narrow bandpass optical filter to filter out any interfering effect if such gas is likely to be present in the sample. The detector is a solid state infrared detector which produces a suitable output signal in response to impinging infrared energy in the range of wavelengths required; and, in the preferred embodiment, a mercury, cadmium telluride (Hg,Cd)Te detector which is highly sensitive to infrared, extremely rapid in its response thereto and produces an output having a high signal-to-noise ratio is used.

In the analysis optical system, the sensitizing cell is one containing the gas of interest and the sample cell, narrow bandpass optical filter and second filter cell are identical to, and preferably common to, those used in the reference system. A single detector is used for both systems.

An electronic signal analyzing system compares the signals produced by the absorption of the infrared energy traversing each of the two systems. The reduction in the total infrared energy traversing both systems accomplished by the narrow bandpass optical filters enhance the relative difference produced by the absorption of infrared energy by the gas of interest in the sample cell. Fluctuations in the signals produced by the reference and sample beams caused by fluctuations in the output of the source or in the detector itself as may occur from time to time do not affect the analyzer of the invention because both beams traverse the same narrow band final filter and are absorbed by a single detector.

BRIEF DESCRIPTION OF THE DRAWING

The lone FIGURE is a schematic representation of an analyzer system in accordance with the invention.

DESCRIPTION OF A REPRESENTATIVE EMBODIMENT

Referring now to the drawing there is shown in schematic representation an analyzer system representative of the type embodying the concepts of the present invention.

The embodiment includes a source of infrared radiation 10, which may be any conventional infrared source capable of delivering infrared radiant energy in the milliwatt range for both reference and sample beams. Thus, such things as a large hot source such as a SiC ignitor, for example, has been successfully used and a smaller hot source, for example, approximately five turns of a 0.25 millimeter diameter Kanthal wire, wound on a 1 mm mandrel, not shown, or the like may be successfully used. Of course, one may also use a large, relatively cool source. A large hot source requires no reflector, a smaller hot source requires a crude reflector and large, relatively cool source requires a good reflector. Means for directing the infrared radiation down a given path in a desired time such as a chopper 11 driven by a synchronized motor 12 is provided to alternately direct the radiation along each of two desired paths.

In the reference optical system A the infrared beam is directed through a neutral filter 13, discussed below, and is deflected into alignment with a reference filter cell 14 in typical fashion as by the use of a mirror 15a. The reference filter cell is typically filled with a gas transparent to infrared radiation such as nitrogen. Beyond the reference filter cell, the reference system contains means to further direct the radiation as required, which may be mirrors 16a and 17a which align the beam for transmission through the remainder of the system. In a similar fashion, infrared radiation in the analysis system B is directed as by a mirror 15b through sensitizing cell 18, which contains a pure specimen of the gas of interest for which the sample is to be analyzed. After traversing the sensitizing cell 18, the analysis beam is directed as by mirrors 16b and 17b such that it is aligned for transmission through the remainder of the analysis system which is coincident with the reference system through its remaining length.

The purpose of the neutral filter 13 is to reduce the total energy of the reference beam by an amount of energy equal to the energy absorbed in sensitizing cell 18 so that both beams have approximately the same total energy at the point where they enter the coincident part of the path. The neutral filter has no infrared spectral structure and therefore it affects the total energy at all wavelengths substantially the same. The sensitizing gas, however, absorbs an equal amount of energy by removing certain infrared wavelengths associated with the characteristic absorption spectrum of that gas.

At this point, then, the reference and analysis beams have substantially the same total energy but quite different spectral structures, i.e., the infrared spectral structure of the reference beam is substantially unchanged from that of the source whereas the spectral structure of the analysis beam is that of the source 10 with the spectrum of the sensitizing gas removed therefrom.

In regard to the use of the neutral filter 13 it may also be stated that because the amount of energy absorbed in the sensitizing cell 18 in relation to the amount of energy provided from the source 10 are relatively constant for any given gas to be analyzed by such a system, that the difference in the radiant energy transmitted by the two beams can also be compensated by other means such as in the electronics of the system which process the detector signal and produce the final readout.

Proceeding further along the optical path, the reference and analysis beams are then alternately caused to be transmitted through the sample cell 19, a filter cell 20, and narrow bandpass optical filter 21 to the detector 22.

It might be noted that the sample cell 19 may be of the continuous flow type wherein the sample gas is continuously flowing in and out of the sample cell 19 or may be an enclosed cell utilizing a sample taken from a sample stream in batchwise fashion at desired time intervals. The general requirements of the sample cell 19 include those desirable for any cell of this type, namely that it be reasonably small in volume, have no leaks, not contain any dead space, be easily cleaned and not react with the sample. The end windows, of course, must be transparent to infrared radiation of the wavelengths at which the sample absorbs. The walls of the sample cell must themselves absorb as little infrared radiation energy as possible. A sample cell 19 having highly reflective interior walls transmits a great deal more infrared energy from the source to the detector and thus is highly desirable. One technique which has been highly successfully used in increasing this reflectance of the interior walls of the sample cell has been to plate them with gold, since gold has a very high infrared reflectance and is chemically inert to most samples analyzed by this method.

The filter cell 20 contains a gas which may interfere with the analysis for the gas of interest. The interfering gas is one having an infrared absorption spectrum which has a fine infrared spectral structure overlapping that of the gas of interest within the narrow band of wavelengths passed by the narrow bandpass optical filter 21. The fine infrared spectral structure is defined as the band of fine absorption lines making up each strong absorption line in the broader infrared absorption spectrum of a gas. Thus the filter cell 20 functions to eliminate the fine structure of the interfering gas from both the analysis and reference systems so that it will not be mistaken for the gas of interest by the detector. If no interfering gas exists or is present in the sample the filter cell 20 may be left empty or eliminated. If a plurality of such gases may be present in the sample, amounts of all of them are introduced into the filter cell 20.

In the above manner interference by gaseous components in the sample other than the gas of interest is eliminated except for gases which have a fine infrared absorption spectrum directly correlated with that of the gas of interest within the designated narrow band. The chances of that occurring are extremely remote. Except in the analysis of certain hydrocarbons, if proper selection of the narrow band optical filter is made in conjunction with the gas of interest to be detected, no constituents normally determined by infrared absorption analysis are known to present such a problem.

The narrow bandpass optical filter 21 must be one passing a narrow band of the infrared spectrum in which the particular gas of interest has at least one strong absorption line.

The use of a narrow bandpass optical filter to concentrate on a particular, very narrow span of wavelengths in both the analysis and reference systems of the analyzer and, more importantly, the attenuation of the spectrum to concentrate on the same narrow band in both systems produces several important advantages in the analyzer of the invention which should be discussed in some detail.

As related more fully below in relation to the detector itself, the quantitative measurement of a gas of interest by the analyzer of the invention depends on the comparison of infrared light-intensity related detector output signals produced by a non-selective detector.

The difference in those signals is related to the reduction in the infrared energy in the reference path produced by absorption due to the presence of some of the gas of interest in the sample. It is well known that comparison of two relatively large values having a small difference therebetween results in a greater source of error than the comparison of two much smaller signals having a relatively greater difference therebetween. Thus, by limiting the band of the infrared spectrum which reaches the detector in both the reference and analysis systems to a very narrow band encompassing one or more strong absorption lines of a gas of interest, not only is the total energy transmitted by both systems considerably reduced but the difference therebetween caused by the absorption of infrared energy due to the presence of the gas of interest in the sample is considerably enhanced in relation to the total values of these measurements. Even in the designated narrow band, however, both the sample and reference systems still transmit sufficient infrared energy to be accurately detected.

An additional distinct advantage is gained by the use of the same narrow bandpass optical filter in both the analysis and reference paths of the analyzer of the invention. Shifts which occur from time to time in the output of the source and in the peak response wavelength of the detector due to temperature changes or other phenomena rarely affect the entire infrared spectrum in the same manner. By narrowing the infrared spectrum passed in both the analysis and reference systems to the same narrow band of wavelengths, such shifts as may occur in the source or in the detector affect the infrared energy in each path in virtually the same manner. This, of course, eliminates the need for any elaborate additions to the device to compensate for such spectral shifts.

As with sample cell 19, reference cell 14, sensitizing gas cell 18 and filter cell 20 should also be of reasonably small volume and should preferrably be permanently sealed to guarantee the integrity of their contents. They must have windows transparent to the desired portion of the infrared spectrum and should have a fairly good reflectance to enhance the amount of infrared energy passed therethrough.

The solid state detector 22 should have a high absorbance in that range of any infrared spectrum in which the particular gas of interest has at least one strong absorption line. One highly successful detector has been found to be the material mercury, cadmium telluride $(Hg,Cd)Te$. Mercury, cadmium telluride photoconductive detectors have been found to be particularly advantageous. In one successful embodiment a $(Hg,Cd)Te$ photoconductive detector having a peak response at 4.8 microns and exhibiting excellent response to infrared wavelengths of between about 1.0 and 5.4 microns was used. The range of successful operation of this particular solid state detector is well within that of the common heteroatomic gases normally analyzed by such devices. For example, wavelengths of interest include 3.3 microns for $CH_4$, 4.3 microns for $CO_2$ and 4.7 microns for $CO$. As with most solid state detecting devices, the $(Hg,Cd)Te$ detector produces a greater signal at a lower temperature, and the signal of such detector is somewhat temperature dependent. Therefore in the operation of an instrument utilizing this detector it may be desirable to operate the detector in a temperature-controlled mode; however, for normal ambient temperature operation it is not necessary to cool the detector in order for it to produce a sufficient signal. The response of the detector is extremely rapid (in the order of a few microseconds) and exhibits an excellent signal-to-noise ratio.

In regard to the analyzer, it should be noted that it is an important aspect of the present invention that in the analysis of a given gas of interest the same detector be used for both the sample and reference beams so that any changes in the output of the detector over a period of time will affect both equally.

The signal produced by the detector 22 is conducted as by conductors 23 and 24 to a suitable signal amplification electronic system 25 is utilized to differentially compare the signals produced by the radiation transmitted through the alternate paths to a final differential reading indicating quantitatively the amount of the gas of interest in the particular sample analyzed. The output of this electronic system 25 may be a meter or a recording device 26 with a provision for zeroing the reading before a sample is introduced and adapted for the particular type of readout desired in terms of type of amount readout and also whether it is continuous meter, chart recorder or other type readout means.

As has been stated, the response of a $(Hg,Cd)Te$ detector is extremely rapid and the frequency at which the analyzer is switched between the reference and analysis systems is quite high. The normal frequency at which the system may be operated is from between about 0.1 to about 10,000 hertz utilizing a conventional electronic amplifying system.

The embodiments of the invention in which an exclusive property or right is claimed are defined as follows:

1. In an apparatus for the selective determination of a gas of interest in a gaseous mixture wherein said gas of interest has a known characteristic infrared absorption spectrum, including a source of infrared radiation, first and second optical systems; said first optical system comprising first filter cell means containing said gas of interest, sample cell means for containing a sample of gas to be analyzed, said second optical system comprising said sample cell, first radiation directing means for directing said infrared radiation through said first optical system, second radiation directing means for directing said infrared radiation through said second optical system, the improvement comprising, in combination:

nonabsorbing optical filtering means for receiving said infrared radiant energy transmitted through either said first or said second optical systems wherein said filtering means passes a selected narrow portion of the infrared spectrum in which said gas of interest has at least one strong absorption line;

single solid state detector means for detecting said infrared radiation transmitted through either said first or second optical systems, wherein said detector means produces first and second electrical signals indicative of the intensity of said infrared radiation received through said first and second optical systems, and signal processing means for determining the quantity of said gas of interest in said gaseous mixture by deriving a comparison output from said first and second electrical signals.

2. Apparatus as claimed in claim 1 wherein said filtering means is a narrow bandpass optical filter.

3. Apparatus as claimed in claim 1 further comprising second filter cell means to filter radiation from both said first and second optical systems, wherein said second filter cell means contains a gas having an infrared absorption spectrum which overlaps that of the gas of interest in the narrow portion of the infrared spectrum passed by said optical filtering means.

4. Apparatus as claimed in claim 1 including compensating means for compensating in said second optical filtering system for infrared energy absorbed by said first filter cell in said first optical system.

5. Apparatus as claimed in claim 1 wherein said detector is a mercury, cadmium telluride detector.

6. Apparatus as claimed in claim 1 further comprising third filter cell means in said second optical system, wherein said third filter cell means contains a gas transparent to infrared radiation.

7. Apparatus as claimed in claim 6 wherein said gas transparent to infrared radiation is nitrogen.

8. Apparatus for selectively determining the presence of a gas of interest in a gaseous mixture wherein said gas of interest has a known characteristic infrared absorption spectrum, the apparatus comprising:

a source of infrared radiation, first and second optical systems, said first optical system comprising first filter cell means containing said gas of interest, nonabsorbing optical filtering means in both said first and second optical systems for passing a selected narrow band of the infrared spectrum wherein said gas to be detected has at least one strong absorption line, sample cell means in both said first and second optical systems for containing a sample of the gas to be analyzed, first radiation directing means for directing said infrared radiation through said first optical system, second radiation directing means for directing said infrared radiation through said second optical system, single solid state detector means for detecting said infrared radiation transmitted through either of said first or second optical systems wherein said detector means produces first and second electrical signals in response to impinging infrared radiation via said first and second optical systems signal processing means for determining the quantity of said gas to be detected in said mixture by deriving a comparison output from said first and second electrical signals.

9. Apparatus as claimed in claim 8 wherein said first and second radiation directing means further comprises a beam chopper and mirror system.

10. Apparatus as claimed in claim 8 further comprising second filter cell means in said second optical system containing a gas transparent to infrared radiation.

11. An apparatus as claimed in claim 10 wherein said gas in said filter cell means is nitrogen.

12. Apparatus as claimed in claim 10 including compensating means in said second optical system for compensating for differences in the total infrared energy transmitted by said first and said second filter cell means.

13. Apparatus as claimed in claim 8 further comprising third filter cell means in both said first and second optical systems for containing a gas having an infrared absorption spectrum which overlaps that of the gas of interest in the narrow band passed by said optical filtering means.

14. An apparatus as claimed in claim 8 wherein said first and second radiation directing means includes means for sequentially directing said radiation along alternate paths.

15. Apparatus as claimed in claim 8 wherein said solid state detector is a photoconductive detector.

16. An apparatus as claimed in claim 15 wherein said solid state detector is a mercury cadmium telluride detector.

* * * * *